(12) United States Patent
St. Louis et al.

(10) Patent No.: US 10,886,020 B2
(45) Date of Patent: Jan. 5, 2021

(54) PREDICTIVE MAINTENANCE SYSTEM AND METHOD FOR 1-WIRE HANDPIECE

(71) Applicant: KAVO DENTAL TECHNOLOGIES, LLC, Charlotte, NC (US)

(72) Inventors: Robert Thomas St. Louis, Charlotte, NC (US); Michael Carl Dunaway, Charlotte, NC (US); Mitchell James Rutledge, Mount Holly, NC (US)

(73) Assignee: KAVO DENTAL TECHNOLOGIES, LLC, Charlotte, NC (US)

( * ) Notice: Subject to any disclaimer, the term of this patent is extended or adjusted under 35 U.S.C. 154(b) by 437 days.

(21) Appl. No.: 15/494,096

(22) Filed: Apr. 21, 2017

(65) Prior Publication Data

US 2018/0307797 A1 Oct. 25, 2018

(51) Int. Cl.
| | |
|---|---|
| *G16H 40/40* | (2018.01) |
| *G01H 17/00* | (2006.01) |
| *G01M 13/04* | (2019.01) |
| *A61C 1/00* | (2006.01) |
| *G06Q 10/00* | (2012.01) |

(52) U.S. Cl.
CPC ........... *G16H 40/40* (2018.01); *A61C 1/0007* (2013.01); *A61C 1/0015* (2013.01); *A61C 1/0053* (2013.01); *A61C 1/0061* (2013.01); *G01H 17/00* (2013.01); *G01M 13/04* (2013.01); *A61C 2204/007* (2013.01); *G06Q 10/20* (2013.01)

(58) Field of Classification Search
None
See application file for complete search history.

(56) References Cited

U.S. PATENT DOCUMENTS

| | | | | |
|---|---|---|---|---|
| 3,582,928 A | * | 6/1971 | Gaertner | G01K 7/021 |
| | | | | 340/522 |
| 5,599,112 A | * | 2/1997 | Klein | F16C 17/04 |
| | | | | 340/648 |
| 5,902,049 A | * | 5/1999 | Heshmat | F16C 17/024 |
| | | | | 384/106 |
| 10,052,172 B2 | * | 8/2018 | Muto | G01R 31/343 |

(Continued)

FOREIGN PATENT DOCUMENTS

| | | |
|---|---|---|
| EP | 2514386 A1 | 10/2012 |
| WO | 2016174187 A1 | 11/2016 |

OTHER PUBLICATIONS

International Search Report and Written Opinion for Application No. PCT/US2018/028431 dated Jul. 11, 2018 (15 pages).

*Primary Examiner* — Lina M Cordero
(74) *Attorney, Agent, or Firm* — Michael Best & Friedrich LLP

(57) ABSTRACT

A predictive maintenance system and method for a dental handpiece includes a condition sensor for sensing a condition of the handpiece to obtain sensor data and providing wired communication of the sensor data and a device identifier from the handpiece to a delivery unit. The system is configured to store sensor data, a device identifier and a time stamp in data logging equipment to obtain a usage history for the handpiece. The system determines a maintenance condition of the handpiece based on the sensor data and/or the usage history of the handpiece. In response to a severity of the maintenance condition, the system provides a preventative maintenance indication of a future failure for the handpiece or stops operation of the handpiece.

5 Claims, 12 Drawing Sheets

(56) References Cited

U.S. PATENT DOCUMENTS

| | | | |
|---|---|---|---|
| 2004/0209223 | A1 | 10/2004 | Beier et al. |
| 2005/0109212 | A1* | 5/2005 | Cattani .................. A61C 17/04 |
| | | | 96/397 |
| 2005/0240312 | A1* | 10/2005 | Terry .................... F25B 49/005 |
| | | | 700/276 |
| 2007/0038206 | A1 | 2/2007 | Altshuler et al. |
| 2008/0014550 | A1* | 1/2008 | Jones .................... A61C 1/0015 |
| | | | 433/114 |
| 2008/0118890 | A1* | 5/2008 | Knopp ..................... A61C 1/12 |
| | | | 433/104 |
| 2008/0120137 | A1* | 5/2008 | Nyholm ................. G16H 10/60 |
| | | | 705/3 |
| 2009/0322541 | A1 | 12/2009 | Jones et al. |
| 2011/0053409 | A1 | 3/2011 | Muto et al. |
| 2014/0072930 | A1* | 3/2014 | Pruckner .............. A61C 1/0007 |
| | | | 433/27 |
| 2014/0134565 | A1* | 5/2014 | Kunisada ............... A61C 19/04 |
| | | | 433/27 |
| 2014/0260707 | A1* | 9/2014 | Megremis ........... G01M 99/008 |
| | | | 73/865.9 |
| 2014/0331753 | A1* | 11/2014 | Wiebrecht ............. G01M 13/04 |
| | | | 73/114.81 |
| 2015/0125809 | A1 | 5/2015 | Pruckner et al. |
| 2015/0150647 | A1* | 6/2015 | Chevalier ............ A61C 1/0015 |
| | | | 433/27 |
| 2017/0035539 | A1* | 2/2017 | Bringley .............. A61C 19/004 |
| 2017/0100015 | A1* | 4/2017 | Mangelberger .... A61B 1/00124 |
| 2017/0116582 | A1* | 4/2017 | Larsen .................... G06Q 10/20 |
| 2018/0038414 | A1* | 2/2018 | Sasao ...................... F16C 41/00 |
| 2019/0023296 | A1* | 1/2019 | Kohler .................. G06Q 10/20 |
| 2019/0047598 | A1* | 2/2019 | Nishimura ................ B61K 9/04 |

* cited by examiner

PREDICTIVE MAINTENANCE SYSTEM AND METHOD FOR 1-WIRE HANDPIECE

BACKGROUND

Embodiments relate to a predictive maintenance arrangement for a dental handpiece.

SUMMARY

One embodiment provides a delivery unit for use with a treatment unit and data logging equipment. In one example, the delivery unit includes a delivery unit controller including an electronic processor, and a power source. The delivery unit includes a power and communication cord having a first end connected to the delivery unit controller and an electric motor coupler including an electric motor that is connected to a second end of the power and communication cord for receiving power and control signals from the delivery unit controller. The electric motor coupler has oriented toward a distal end at least one from a group consisting of: connecting pins, connecting pin receiving ports, and contact rings. The delivery unit includes a handpiece having a distal end with an end cap and a proximal end with an aperture for receiving at least a portion of the electric motor coupler. The handpiece includes a condition sensor for sensing a condition of the handpiece and at least one electrical wire connecting the condition sensor to at least one from a group consisting of connecting pins, connecting pin receiving ports, and contact rings that are provided at or near the proximal end of the handpiece for mating with at least one from the group consisting of: connecting pins, connecting pin receiving ports, and contact rings disposed toward a distal end of the electric motor coupler. The electronic processor is configured to: provide electrical power via the power and communication cord to the electric motor, receive sensor data from the condition sensor via the power and communication cord, and store the sensor data in the data logging equipment with a timestamp.

Another embodiment provides a method of providing predictive maintenance for a dental handpiece or component thereof. In one example, the method includes sensing a condition of the handpiece with a condition sensor to obtain sensor data, providing wired communication of the sensor data and a device identifier from the handpiece to a delivery unit, and storing the sensor data, the device identifier and a time stamp in data logging equipment to obtain a usage history for the handpiece. The method further includes determining a maintenance condition of the handpiece based on the sensor data and/or the usage history of the handpiece, and in response to a severity of the maintenance condition, providing a preventative maintenance indication of a future failure for the handpiece.

Another embodiment provides a method of providing predictive maintenance for a dental handpiece or component thereof. In one example, the method includes sensing a condition of the handpiece with a condition sensor to obtain sensor data, providing wired communication of the sensor data and a device identifier from the handpiece to a delivery unit, and storing the sensor data, the device identifier and a time stamp in data logging equipment to obtain a usage history for the handpiece. The method further includes determining a maintenance condition of the handpiece based on comparing the sensor data and/or the usage history of the handpiece with sensor data and/or usage history for other handpieces, and in response to a severity of the maintenance condition, providing a preventative maintenance indication of a future failure for the handpiece.

Other aspects will become apparent by consideration of the detailed description and accompanying drawings.

DETAILED DESCRIPTION

Before any embodiments are explained in detail, it is to be understood that they are not limited in their application to the details of construction and the arrangement of components set forth in the following description or illustrated in the following drawings. Other embodiments are possible and embodiments explained are capable of being practiced or of being carried out in various ways.

Figure 1:
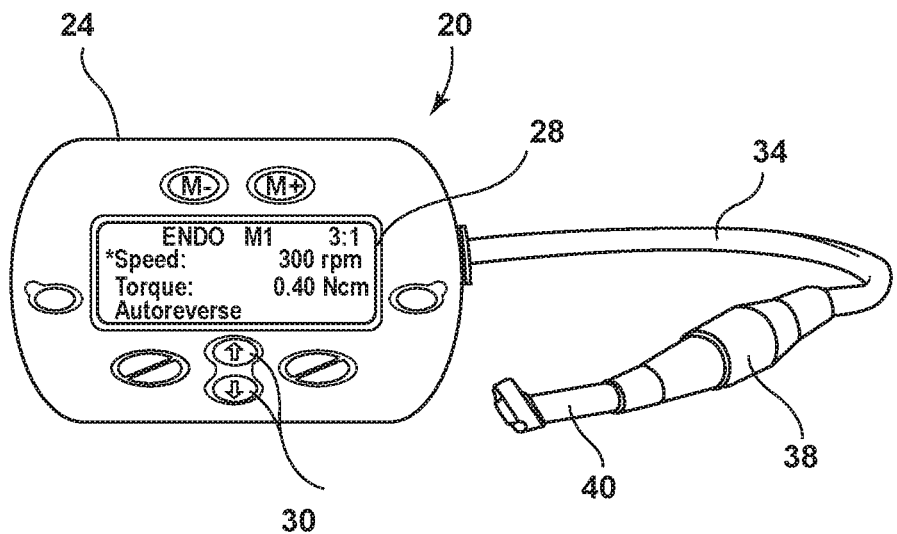
FIG. 1 is a front view of an embodiment for a stand-alone dental handpiece system.

FIG. 1 shows a stand-alone dental handpiece system 20 having a motor controller 24 with a display 28 and push buttons 30. In the example illustrated, the dental handpiece system 20 includes a communication and power cord 34 that connects at a first end to the motor controller 24 and at a second end to an electric motor coupler 38. A handpiece 40 mounts to or mates with the electric motor coupler 38. The handpiece 40 generally receives a portion of the electric motor coupler 38. In some embodiments, the display 28 is a touchscreen that receives inputs by a user. In some embodiments, the electric motor coupler 38 is separable from the communication and power cord 34, along with the handpiece 40. The dental handpiece system 20 is considered a delivery unit that includes a single handpiece 40 for stand-alone operation. Other embodiments include a delivery unit having multiple handpieces.

Figure 2:
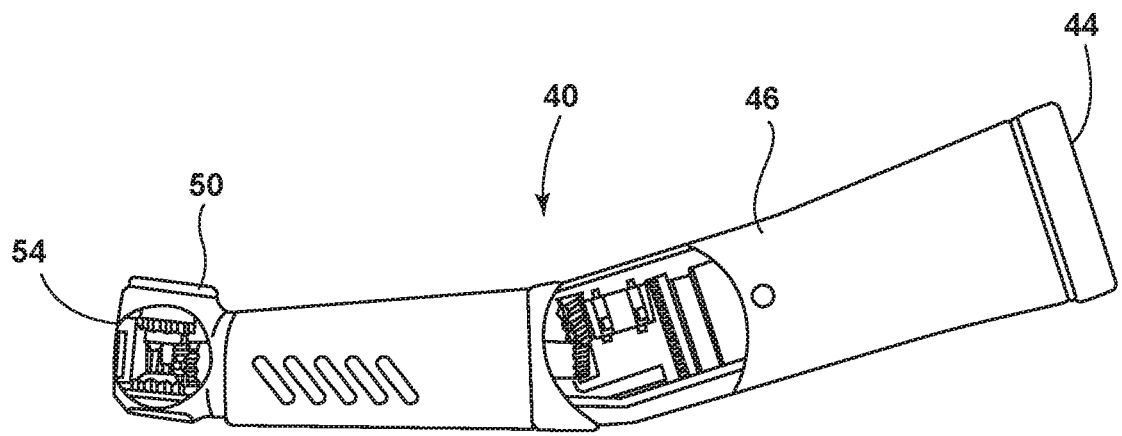
FIG. 2 is a perspective, partially-cutaway view of a handpiece.

FIG. 2 shows a partial cutaway view of the handpiece 40. In the example illustrated, a proximal end 44 of the handpiece 40 has an opening for receiving and mating with an electric motor of the electric motor coupler 38. A housing 46 of the handpiece 40 has a central cut-away that enables viewing of shafts and gears for the handpiece 40. Likewise, an end cap 50 at a distal end 54 of the handpiece 40 has a cut-away that shows shafts and gears.

Figure 3:
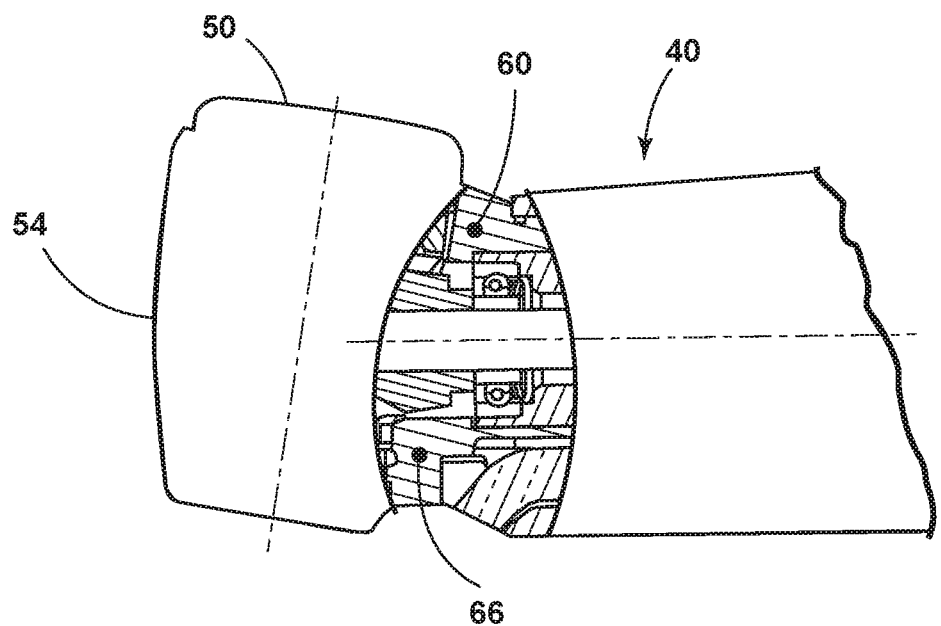
FIG. 3 is a partially-cutaway view of a distal end of the handpiece of FIG. 2.

FIG. 3 shows a partial cut-away view of a distal end 54 of the handpiece 40. FIG. 3 shows a first temperature sensor 60 disposed at the distal end 54 of the handpiece and adjacent the end cap 50 and away from a path for providing air/water. The temperature sensor 60 is disposed near bearings of the shafts and gears of the handpiece 40 to act as a bearing temperature sensor. The bearing temperature sensor 60 is glued or otherwise secured within the handpiece 40 and at least one wire extends therefrom toward the proximal end 44 of the handpiece. The proximal end 44 has an aperture or other receiving structure.

In the embodiment shown in FIG. 3, a second temperature sensor 66 is disposed at the distal end 54 of the handpiece and near a path for providing air/water. The second temperature sensor 66 is also disposed near bearings of the shafts and gears of the handpiece 40 and may act as a bearing temperature sensor. The temperature sensor 66 is glued or otherwise secured within the handpiece 40 and at least one wire extends therefrom toward the proximal end 44 of the handpiece. While two temperature sensors 60, 66 are illustrated in FIG. 3, embodiments may include a single temperature sensor or more than two temperatures sensors.

Figure 4:
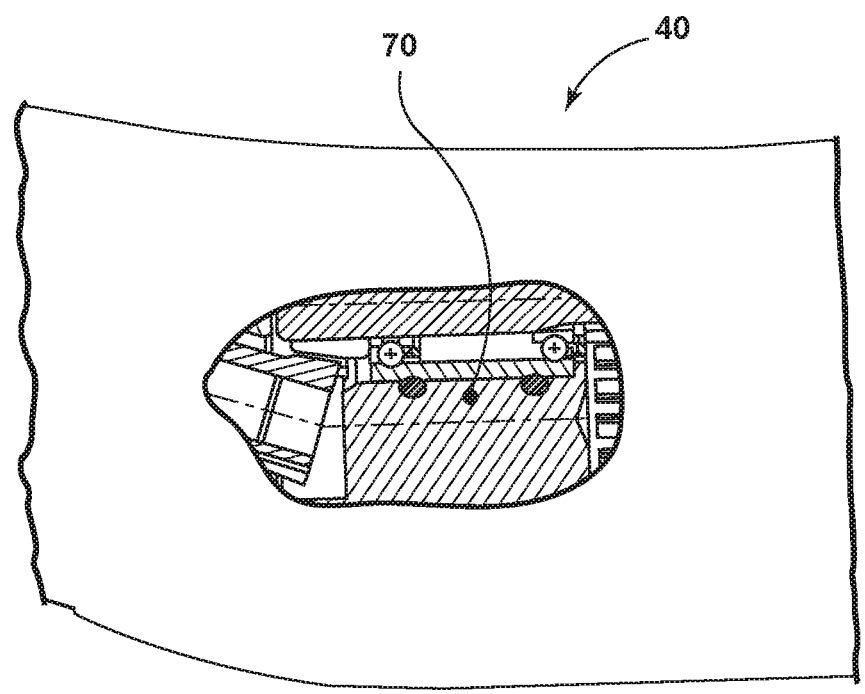
FIG. 4 is a partially-cutaway view of a central portion of the handpiece of FIG. 2.

FIG. 4 shows a partial cut-away view of a central portion of the handpiece 40. A temperature sensor 70 is disposed near bearings of a shaft that accounts for the contra-angle of the handpiece 40 as shown in FIG. 2. The temperature sensor 70 is glued or otherwise secured within the handpiece 40 and at least one wire extends therefrom toward the proximal end 44 of the handpiece.

Figure 5:
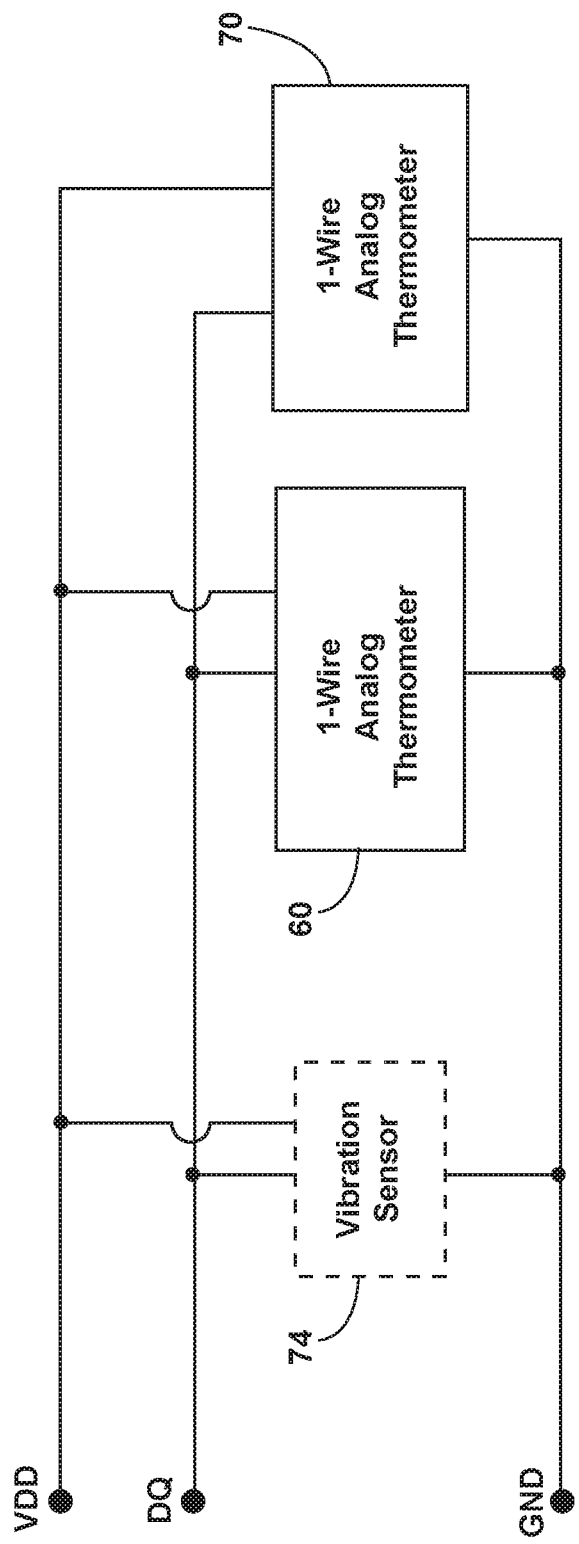
FIG. 5 is a schematic of the handpiece of FIG. 2.

FIG. 5 shows a 1-wire embodiment for two temperatures sensors 60, 70 that are 1-wire analog thermometers. In FIG. 5, a voltage $V_{DD}$ is provided by an electrical wire to each temperature sensor 60, 70 and each temperature sensor (thermometer) is connected to ground GND. The temperature sensors 60, 70, each provide a unique identifier and a temperature value on a communication wire DQ. In FIG. 5, the temperature sensors 60, 70 both share the communication electrical wire DQ, the ground wire GND and a voltage source wire $V_{DD}$. The temperature sensors 60, 66, and 70 shown in FIGS. 3 and 4 have different addresses or unique identifiers. Each sensor 60, 66, and 70 provides a temperature value associated with its address. This information may be used to monitor the handpiece 40 and is processed (as is explained in greater detail below) to provide one or more predictive maintenance conditions or evaluations.

In another embodiment, parasitic power is also supplied to the temperature sensor 70 via the communication wire DQ. Thus, a voltage source electrical wire $V_{DD}$ is not needed and a two wire arrangement results for multiple sensors 60, 70. In an additional embodiment, the ground wire GND is not needed as the temperature sensors 60, 70 and the housing 46 are effectively connected to ground when secured to the motor coupler 38. Thus, one embodiment includes one electrical wire for providing sensor data from multiple condition sensors as a 1 wire arrangement.

Additional condition sensors sharing a communication wire DQ are contemplated. FIG. 5 includes an alternative embodiment having an additional vibration sensor 74 shown in broken line that is disposed in the handpiece 40 to sense vibration and provide vibration data. In another embodiment, an acoustic microphone is provided in the handpiece 40 to obtain acoustic data. Thus, additional condition sensors are contemplated. The condition sensors each have a different address or unique identifier for monitoring the handpiece 40 to provide sensor data for a predictive maintenance condition. The unique identifier ensures that the sensor data is stored for that unique sensor for the predictive maintenance condition.

Further, the handpiece 40 has a handpiece unique identifier for specific identification of the handpiece. Thus, sensor data from the sensors is identified and may be stored with the correct handpiece. In one embodiment, the device identifier includes a microchip having unique identifier data for the handpiece 40. The microchip is similar to the 1-wire arrangements shown in FIG. 5 that communicate with an electronic processor. Thus, the device identifier is connected by a 1-wire arrangement on one electrical wire to provide sensor data and the device identifier to the electronic processor for processing and storing.

In another embodiment, the unique device identifier is combined with the condition sensor instead of the handpiece itself. The result is similar. Sensor data is associated with a unique condition sensor and the particular handpiece 40 of interest and may be stored in data logging equipment with the appropriate association.

Handpiece System

Figure 6:
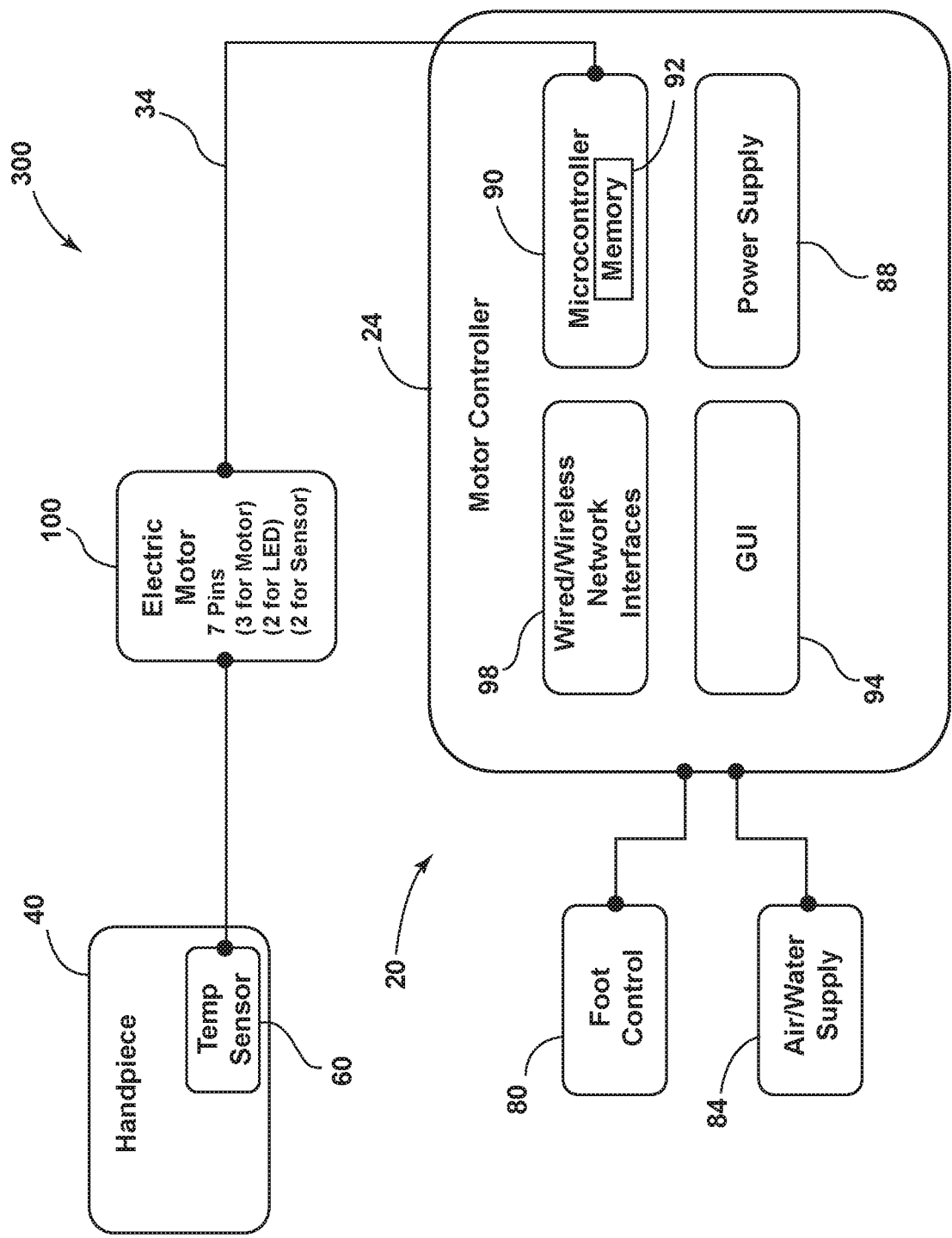
FIG. 6 is a block diagram of the handpiece system of FIG. 1.

FIG. 6 shows the dental handpiece system 20, including a foot control 80 and an air/water supply 84. The motor controller 24 includes a power supply 88, such as a rechargeable battery and/or an electrical lead to a wall outlet or other power source.

The motor controller 24 includes an electronic processor, such as a microcontroller 90 with a memory 92. In some embodiments, the electronic processor is a microprocessor, an application-specific integrated circuit ("ASIC"), or other suitable electronic processing device having a memory. In some embodiments, the memory 92 is a non-transitory computer-readable medium including random access memory ("RAM"), read-only memory ("ROM"), or other suitable non-transitory computer-readable medium.

The motor controller 24 includes a graphical user interface (GUI) 94 for displaying information. The GUI 94 corresponds to the display 28 and push buttons 30 in FIG. 1. In this embodiment, the GUI 94 is a touchscreen to receive touch inputs. Further, the motor controller 24 includes wired and/or wireless network interfaces 98. Examples of such interfaces includes wired interfaces such as an Ethernet module, although other WAN and LAN modules may be used. Suitable wireless interfaces include transceivers that may be configured to communicate in accordance with BLUETOOTH protocol, near-field communications (NFC) protocols, a radio frequency (RF) protocol, Wi-Fi protocol, or other suitable wireless protocols. The network interfaces 98 connect at least the foot control 80 and the GUI 94 to the microcontroller 90.

Other embodiments include direct wired connections from the motor controller 24 to various devices, various mid and long range wireless connections, including connections to various computer networks.

The motor controller 24 of the embodiment shown in FIG. 6 is configured to provide power to and receives information from an electric motor 100 disposed in the electric motor coupler 38 or as a separate component that attaches to the electric motor coupler 38. Thus, in one embodiment the communication and power cord 34 has at least eleven wires connecting the motor controller 24 to the electric motor 100. Three wires provide power (three motor phases U, V, W) to operate the electric motor 100. Another two wires are for at least one light emitting diode (LED) to provide illumination projecting from near the distal end of the handpiece 40. In one embodiment, an additional five wires are connected to sensors to determine the position and movement (operation) of the electric motor 100. In one embodiment, the sensors are two or more Hall effect sensors mounted about an internal driven shaft of the electric motor that detect a magnet secured to the internal shaft to determine position and rotational speed of the internal shaft. The position and movement of the shaft of the electric motor 100 sensed by the Hall effect sensors are provided to the motor controller 24. Finally, in one embodiment, one or more wires are provided for connection to the temperature sensor(s) 60, 66, 70 or vibration sensors, such as acoustic sensors, disposed in the handpiece 40. As shown in FIG. 5, from one to three wires $V_{DD}$, DQ, GND may extend from the electric motor 100 or electric motor coupler 38 to join with the handpiece 40.

In another embodiment, the motor controller 24 further includes an ambient air temperature sensor and a humidity sensor for sensing conditions within a room containing the treatment unit 200. In other embodiments, the ambient air temperature sensor and the humidity are mounted on the handpiece 40 or the electric motor coupler 38.

In one embodiment, the electric motor coupler 38 or the electric motor 100 has oriented toward a distal end at least one from a group consisting of: connecting pins, connecting pin receiving ports, and contact rings that join to and connect with an end of the one, two or three wires provided to join to the handpiece 40. In one embodiment, the electric motor 100 and/or the electric motor coupler 38 are provided with arrangements as disclosed in U.S. patent application Ser. No. 15/456,227, filed Mar. 10, 2017, titled "Powered Coupler for Dental Handpiece", the entire disclosure of which is hereby incorporated by reference.

The proximal end of the handpiece 40 shown in FIGS. 1 and 6 has at least one condition sensor, such as the temperature sensors 60, 66, 70, connected by at least one wire to at least one from a group consisting of connecting pins, connecting pin receiving ports, and contact rings that are provided at or near the proximal end of the handpiece for mating with at least one from a corresponding group consisting of: connecting pins, connecting pin receiving ports, and contact rings disposed toward a distal end of the electric motor coupler 38. Other communication methods and structures provided between the handpiece 40 and the electric motor coupler 38 are contemplated.

Treatment Unit

Figure 7:
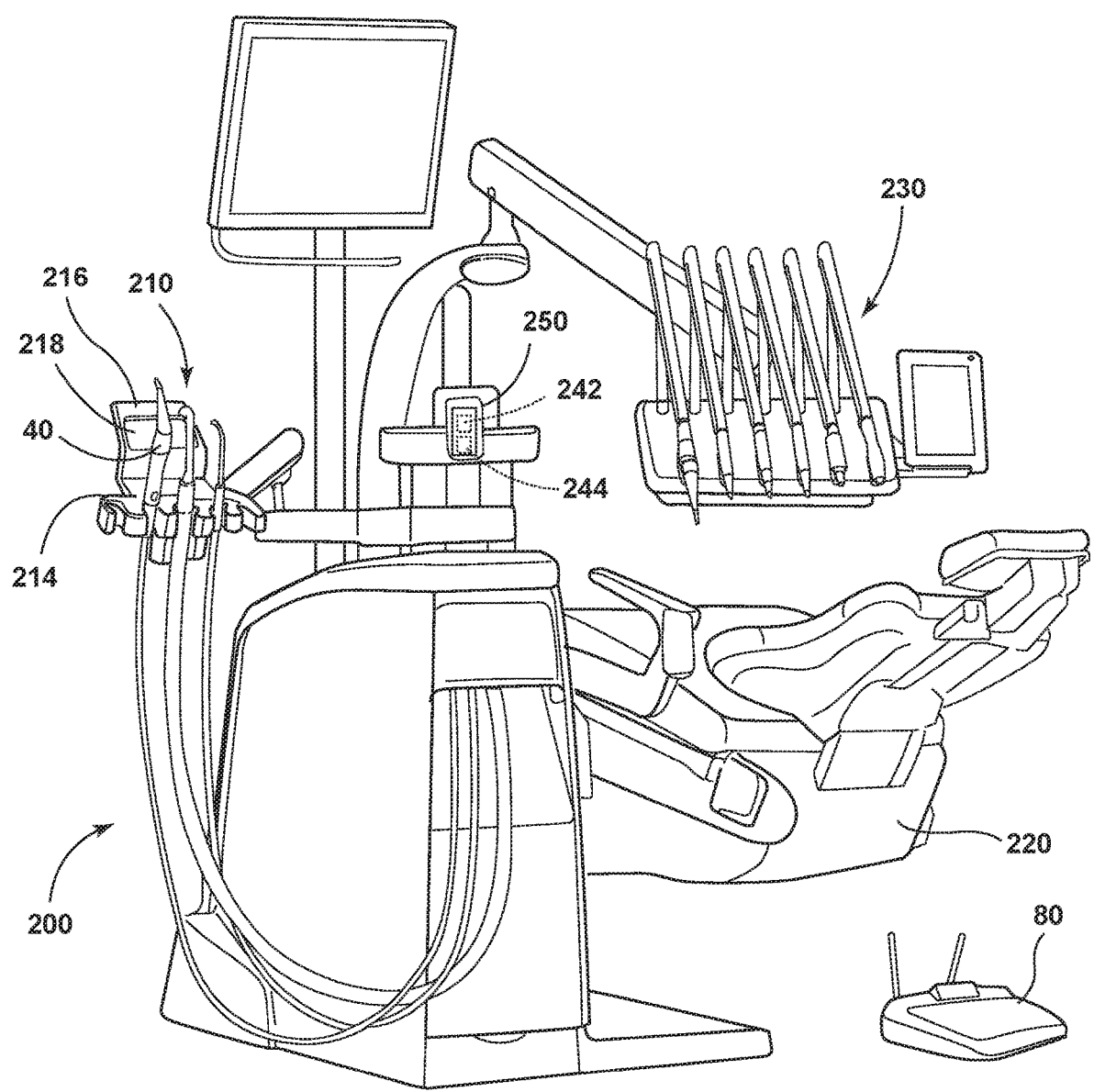
FIG. 7 is a perspective view of an exemplary treatment unit.

FIG. 7 shows one embodiment of a treatment unit 200 that utilizes the handpiece 40 as a part of a delivery unit 210 that supports multiple handpieces. The delivery unit 210 includes a tray 214 with holders formed therein for receiving and storing multiple handpieces when not in use. The delivery unit includes an electronic controller 216 having a graphical user interface, such as a touchscreen 218 for controlling the handpiece. The treatment unit 200 includes a powered chair 220. The treatment unit 200 includes an additional delivery unit 230 that supports multiple handpieces.

The delivery unit 210 is operated to provide power to the handpiece 40 and to sense data from sensors 60, 66, 70 in the handpiece 40 in a similar manner as set forth above for the handpiece system shown in FIGS. 1 and 6. For instance, in one embodiment the delivery unit 210 includes all of the components of the motor controller 24 shown in FIG. 6, including the foot control 80 illustrated in FIG. 7.

In some embodiments, the treatment unit 200 includes one or more external sensors. The external sensors include an ambient air temperature sensor 242 and a humidity sensor 244 to obtain and store temperature and humidity values for a room containing the treatment unit 200. In one embodiment, the sensors 242, 244 are disposed in a single housing 250 and share an electronic processor and a communication link to provide or transmit ambient air temperature data and humidity data. Thus, the sensors 242, 244 are external sensors separate from the handpiece 40.

Communication Arrangement

Figure 8:
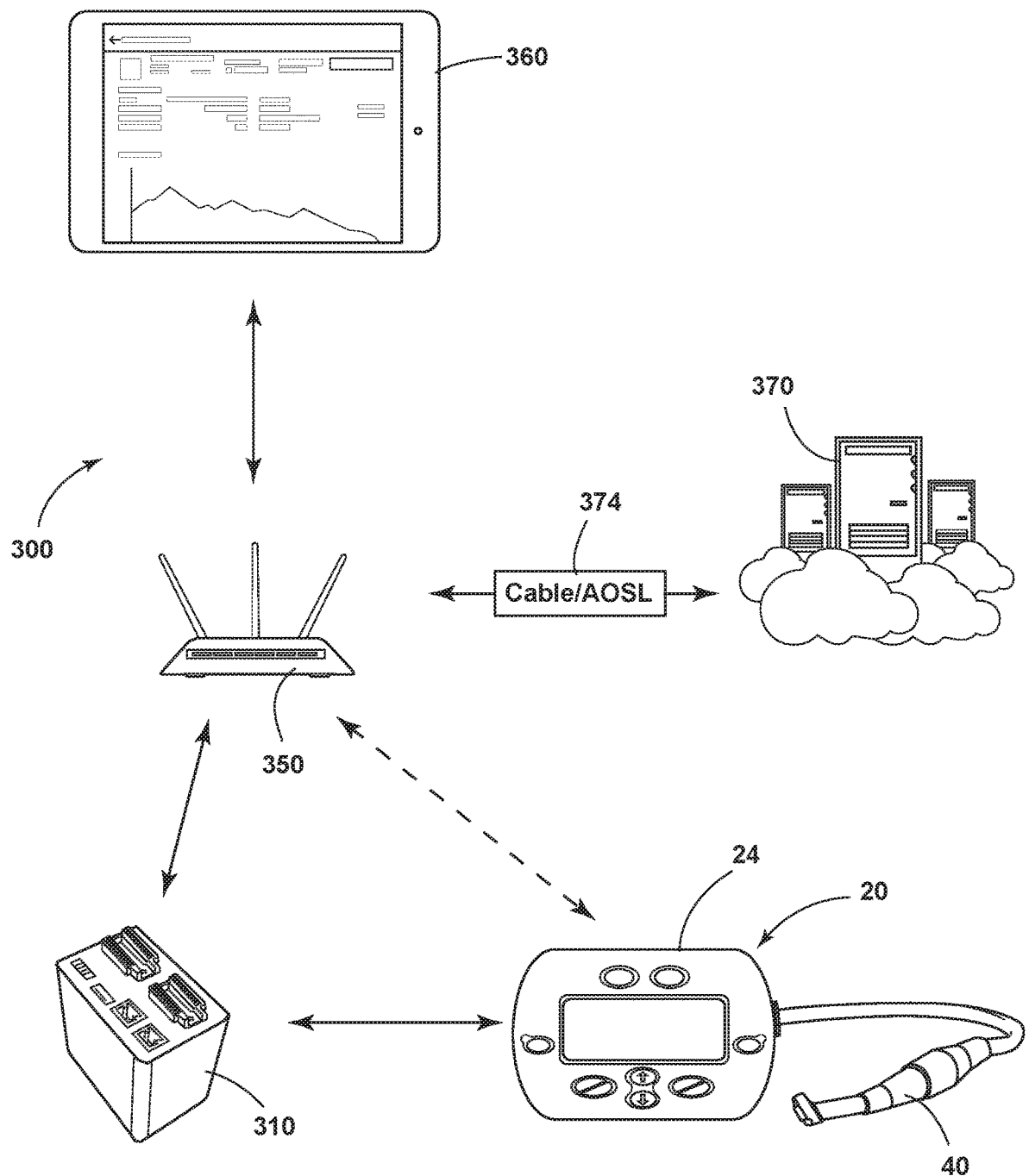
FIG. 8 is a block diagram of communication between components of a treatment unit, including a dental handpiece system, a treatment unit logging computer, a portable universal controller and a cloud computer via a network access point.

FIG. 8 shows one embodiment of a communication diagram 300 that includes a delivery unit, such as the stand-alone handpiece system 20 shown in FIGS. 1 and 6. The stand-alone handpiece system 20 includes wired and/or wireless network interfaces 98, for wired communication or wireless communication with a data logging equipment 310, or for communication via a network access point 350 with the data logging equipment to log sensor data with a timestamp or time marker. The network access point 350 is capable of providing communication and data access to various computer networks.

The network access point 350 shown in FIG. 8 communicates with or links the stand-alone handpiece system 20, the data logging equipment 310, a portable universal controller 360, and a cloud computer 370 or cloud server via a connection 374. In various embodiments, the communication links between the elements shown in FIG. 8 may include wired connections, and various wireless connections, for example BLUETOOTH, NFC, and Wi-Fi connections.

In another embodiment, the data logging equipment 310 shown in FIG. 8 is a non-transitory memory of a delivery unit controller of a delivery unit, such as the motor controller 24. In one embodiment, the data logging equipment is a non-transitory memory associated with or part of the cloud computer 370 or cloud server.

In one embodiment, ambient air temperature data and humidity data are communicated by an electronic processor to the data logging equipment 310 in a wireless or wired arrangement.

Treatment Unit and Handpiece Operation

Figure 9:
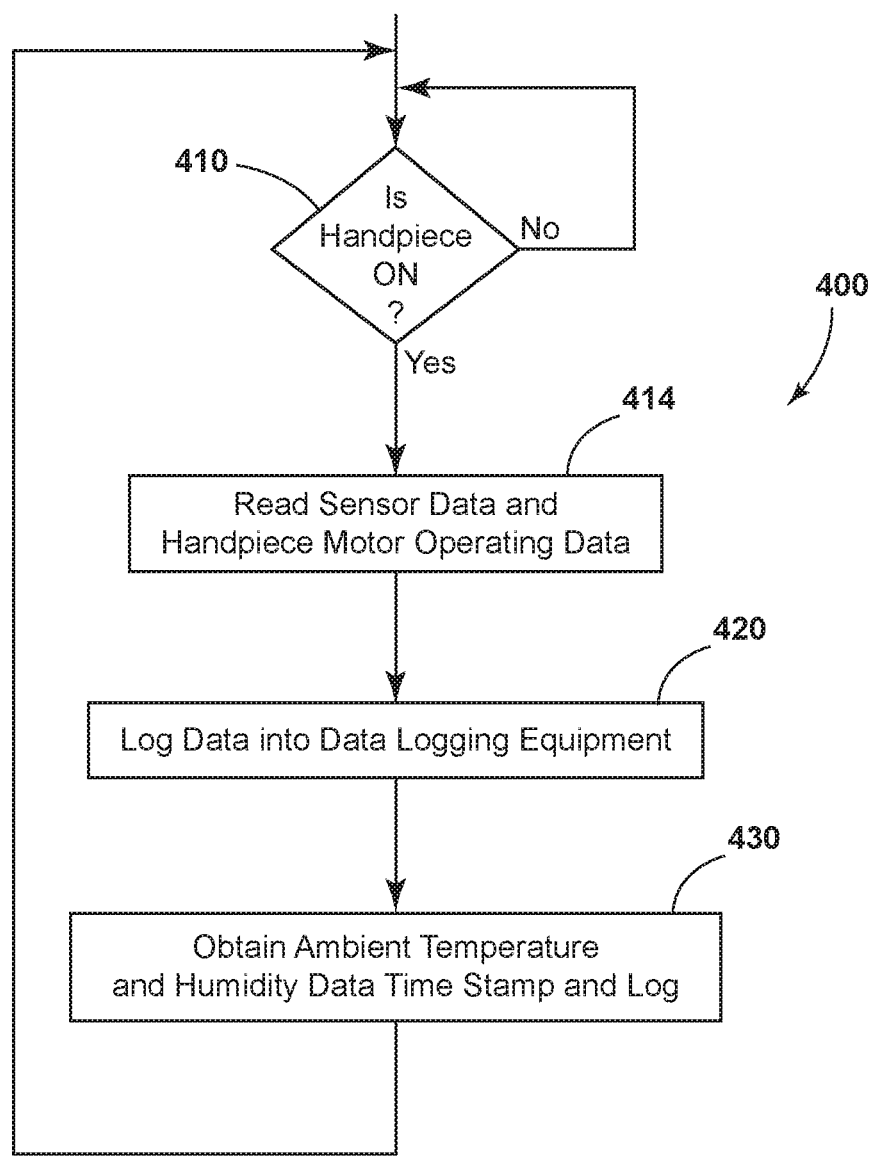
FIG. 9 is a flowchart of a method for storing sensor data for a handpiece.

One embodiment of a method of monitoring operation of the handpiece 40 is shown in the flow chart 400 in FIG. 9. In the example provided, the motor controller 24 determines whether the handpiece 40 is powered for usage (step 410). If no power is being provided to the handpiece 40, even in an idle state, the program executed by the microcontroller 90 of the motor controller 24 returns back to step 410 and periodically repeats the step of determining whether power is received (step 410) shown in FIG. 9. In another embodiment, a switch or relay directly provides a signal to the microcontroller 24 when power is received.

When the handpiece 40 is powered in this embodiment, the microcontroller 90 reads sensor data from the sensors 60, 66, 70 of the handpiece 40 and provides the sensor data to the data logging equipment 310, along with handpiece motor operating conditions that include motor speed, torque, position and load (step 414). Then, all of the data and information is logged by the data logging equipment 310 with time stamps or time markers (step 420). Thus, reading the data later, both the time and data values are available for calculations and comparisons.

Separately in one embodiment, ambient air temperature data and ambient humidity data are provided from an ambient air temperature sensor 242 and a humidity sensor 244 to the data logging equipment 310, which periodically logs the temperature and humidity values with time stamps or time markers (step 430). Thus, both the time and data values for the sensor data are available for calculations and comparisons. These operations are performed independently of the motor controller 24, as the temperature and humidity data is sent separately to the data logging equipment 310. The data logging equipment 310 logs the temperature and humidity data for the handpiece 40 that is currently in use and providing data thereto.

In another embodiment, the ambient air temperature sensor 242 and the humidity sensor 244 are provided with the motor controller 24 and the air temperature data and the humidity data are also sensed by the microcontroller at step 414. Then the ambient air temperature data and the ambient humidity data are logged by the data logging equipment 310 with the other data at step 420.

Thereafter, the method returns to step 410 and the steps are repeated and sensor and motor data is logged during operation of the handpiece 40 and for conditions of a room with the treatment unit 200. The method steps shown in FIG. 9 can be executed in any order.

Execution of the flow chart 400 shown in the embodiment of FIG. 9 creates an operating history or usage history for the handpiece 40 that is stored in the data logging equipment 310. The history includes handpiece operating speeds, operating times, usage time, handpiece temperature data, along with ambient air temperature and humidity conditions. Additional embodiments include rate of temperature increase, thermal time constants, power consumption data, electric motor torque data, axially applied loads to the handpiece motor and radially applied loads. Torque is determined from motor current and rotational speed, revolutions per minute (rpm) of the shaft of the electric motor 100.

Prediction of Handpiece Maintenance—Weighted Values

Figure 10:
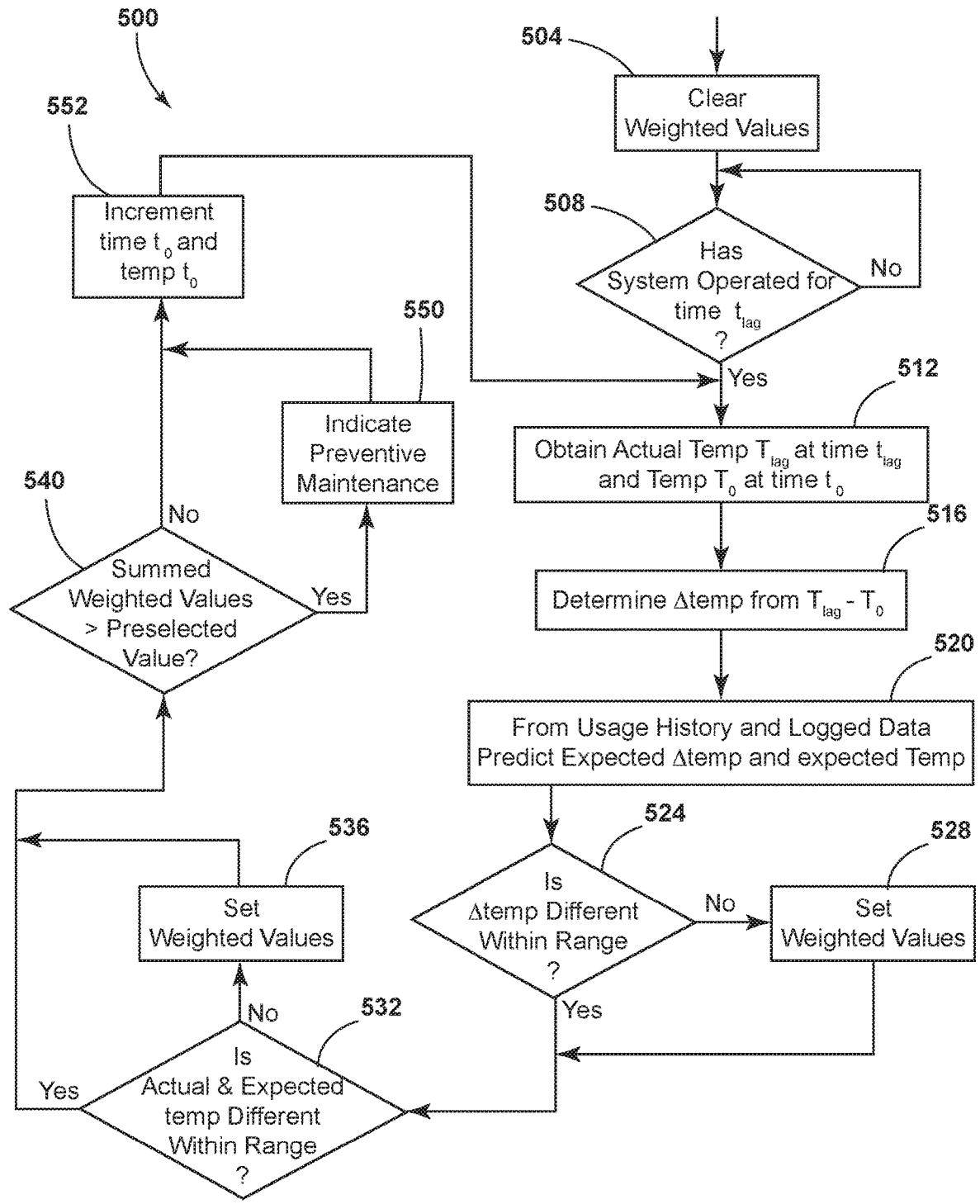
FIG. 10 is a flowchart of a method for comparing sensor data with past sensor data of a handpiece to provide predictive maintenance.

A processor associated with one or more of the motor controller 24, a delivery unit 210, 230, a cloud computer 370, a portable universal controller 360, the treatment unit 200 or another device operates to execute the method shown in FIG. 10. The flow chart 500 shown in FIG. 10 represents a method of predicting a failure of a bearing corresponding to one bearing temperature sensor 60, 66, 70 of the handpiece 40, or a component thereof.

In the embodiment of FIG. 10, previously stored weighted values are cleared when the method starts to execute (step 504). The handpiece 40 operates for a predetermined time $t_{lag}$ before the method begins making comparisons (step 508). During this time period, however, the data logging equipment 310 is logging bearing temperature data for the bearing temperature sensor 60, 66, 70 and other sensor data available to the processor carrying out the method as shown in FIG. 9.

After a predetermined time interval ($t_{lag}$), the temperature ($T_{lag}$) is obtained (step 512). A change of temperature is obtained by subtracting the temperature from the beginning of handpiece operation ($T_0$) at time ($t_0$) from the temperature at time $t_{lag}$ resulting in $T_{lag}-T_0$ (step 516).

In one embodiment, the processor utilizes the usage history of the handpiece electric motor 100, ambient temperature, ambient humidity and temperature sensor value at time $t_0$ to determine an expected change in temperature and an expected temperature at time $t_{lag}$ (step 520). The expected change in temperature is compared with the actual change of temperature (step 524). When the change of temperature is outside of a given range for a given temperature sensor, for example, the actual temperature difference is much greater than the expected temperature difference, a weighted value is set (step 528). In one example, the weighted value is directed to a predicted bearing failure. The weighting values account for a large difference in the changes in temperature as compared to a predicted range of temperature change values. Once the weighted value is set, the program advances to step 532. In one embodiment, when the change of temperature is within a predetermined range, the program bypasses step 528 and continues to step 532. In another embodiment, some weighted values are omitted based on certain operating conditions, such as an excessive load applied to the handpiece motor, spray water turned off for the handpiece 40 or other conditions.

The method then determines whether the difference between the actual temperature and the expected temperature are within a predetermined range (step 532). If the temperature difference is significantly different than predicted (outside the range), the method advances to set another weighted value (step 536). In one example, the weighted value is weighted based on the difference between the temperatures and a look-up table or equation providing weighted value differences. When the weighted value is set, the method advances to step 540. When the temperature difference is within the predicted range, the method advances from step 532 to step 540.

A sum of weighted values is compared to a preselected value "Z" from a look-up table or from an equation that indicates that there is an anomaly for the temperature corresponding to the bearing. In one embodiment, the preselected value is selected based in part on the ambient temperature and other factors. If the comparison indicates that there is an anomaly in the temperature, the method advances to step 550. An indication is provided that preventive maintenance is required for the handpiece 40 (step 550). The indication is provided on the display 28 of the dental handpiece system 20 or on the display of another delivery unit 210 provided with the treatment unit 200. The indication generally is specific to the exact shaft bearing requiring repair. An audible warning also can be provided by the treatment unit 200.

Thereafter, the method increments the values for time $t_0$ and time $t_{lag}$ (step 552). Then, the method advances to step 512 and repeats the process with the incremented time values. Upon end usage of the handpiece 40, the method shown in FIG. 10 discontinues operation.

While not discussed in detail, in certain embodiments the method shown in FIG. 10 repeatedly executes. In some embodiments, over time, the oldest weighted values are reduced, deducted or no longer summed for comparison with the preselected value "Z" (step 540). The underlying sensor and handpiece data, however, along with the weighted values, are stored or remain stored by the data logging equipment 310 as usage history. Other alternatives are contemplated.

The arrangement of FIG. 10 is directed to one sensor of a plurality of sensors provided on the handpiece 40. Other sensors may be used in similar methods. In addition, multiple sensors of temperature, vibration, and other conditions are provided in other embodiments for determining a preventive maintenance condition of a handpiece 40.

Alarm Levels

Figure 11:
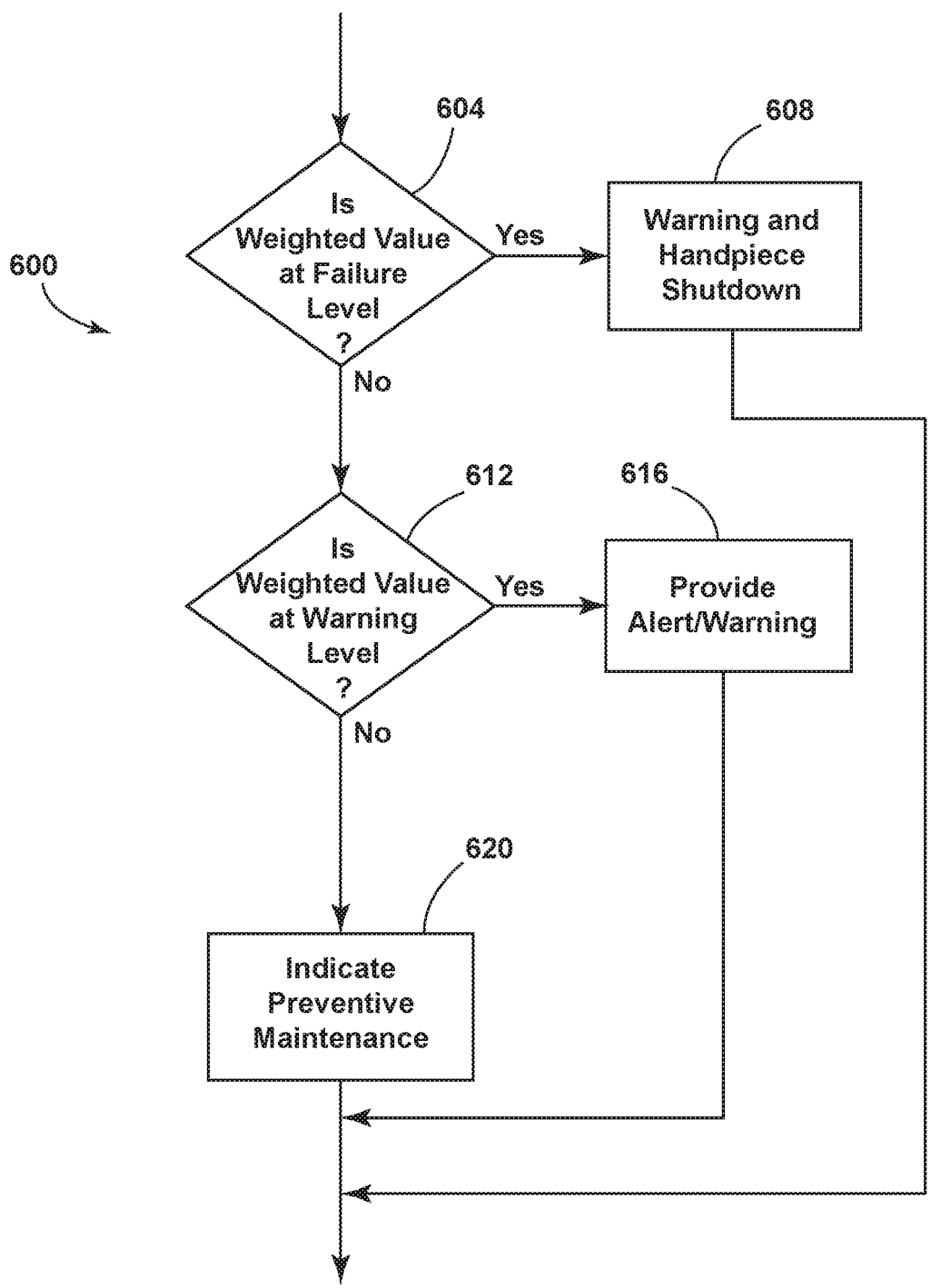
FIG. 11 is a flowchart of a method for providing alarm levels for sensor data from a handpiece.

The arrangement of FIG. 11 shows a modification for method step 550 of the method of FIG. 10. Step 550 is replaced with the method illustrated in the flow chart 600 that provides separate select indications and/or handpiece control. The method provides alarm levels and functions for the weighted value depending on the condition sensed. For instance a weighted value for a bearing temperature obtained in the arrangement of FIG. 10 triggers one from a group consisting of: 1) a preventative maintenance indication of a future failure for the handpiece 40 (such as a 40%-90% wear of a bearing life expectancy); 2) a maintenance warning of more immediate expected failure of a bearing of the handpiece, such as overheating, (such as 90% or more of expected bearing life expectancy); and 3) a disabling of operation of the handpiece 40 to be provided depending on increased severity of the weighted value corresponding, for example, to an increased bearing temperature that corresponds to bearing failure.

More specifically, FIG. 11 shows initially comparing a weighted value corresponding to temperature to a failure level value (step 604) for a handpiece 40. When the weighted value is at or beyond a failure level (step 604), the method advances to provide an audible and/or visual warning, and control the motor controller 24 to stop and prevent operation of the handpiece 40 (step 608). Thus, the handpiece 40 is shut down. Thereafter, the steps of FIG. 11 are completed.

When the weighted value is not great enough to require handpiece shutdown (decision step 604), the method advances to another decision step to determine whether the weighted value is at a warning level (decision step 612). When the weighted value is at or greater than a warning level, the method advances to provide a warning with a graphical user interface and/or loudspeaker (step 616), such as for overheating of a bearing. Thus, in response to a severity of the maintenance condition such as temperature, the arrangement provides a preventative maintenance warning of a rapidly approaching future failure for the handpiece 40. Thereafter, the steps of FIG. 11 are completed.

When the weighted value is not great enough to require a warning (step 612), the method advances to indicate preventive maintenance by providing a maintenance indication (step 620). The preventive maintenance indication allows a user to account to future maintenance for the handpiece 40 (for example, 40%-60% wear corresponding to a bearing life expectancy).

In one embodiment, the weighted value is dependent mainly on the sensed temperature of a given bearing. Other arrangements are contemplated based on other sensed conditions, such as vibration.

Thermal Equations Embodiment

Figure 12:
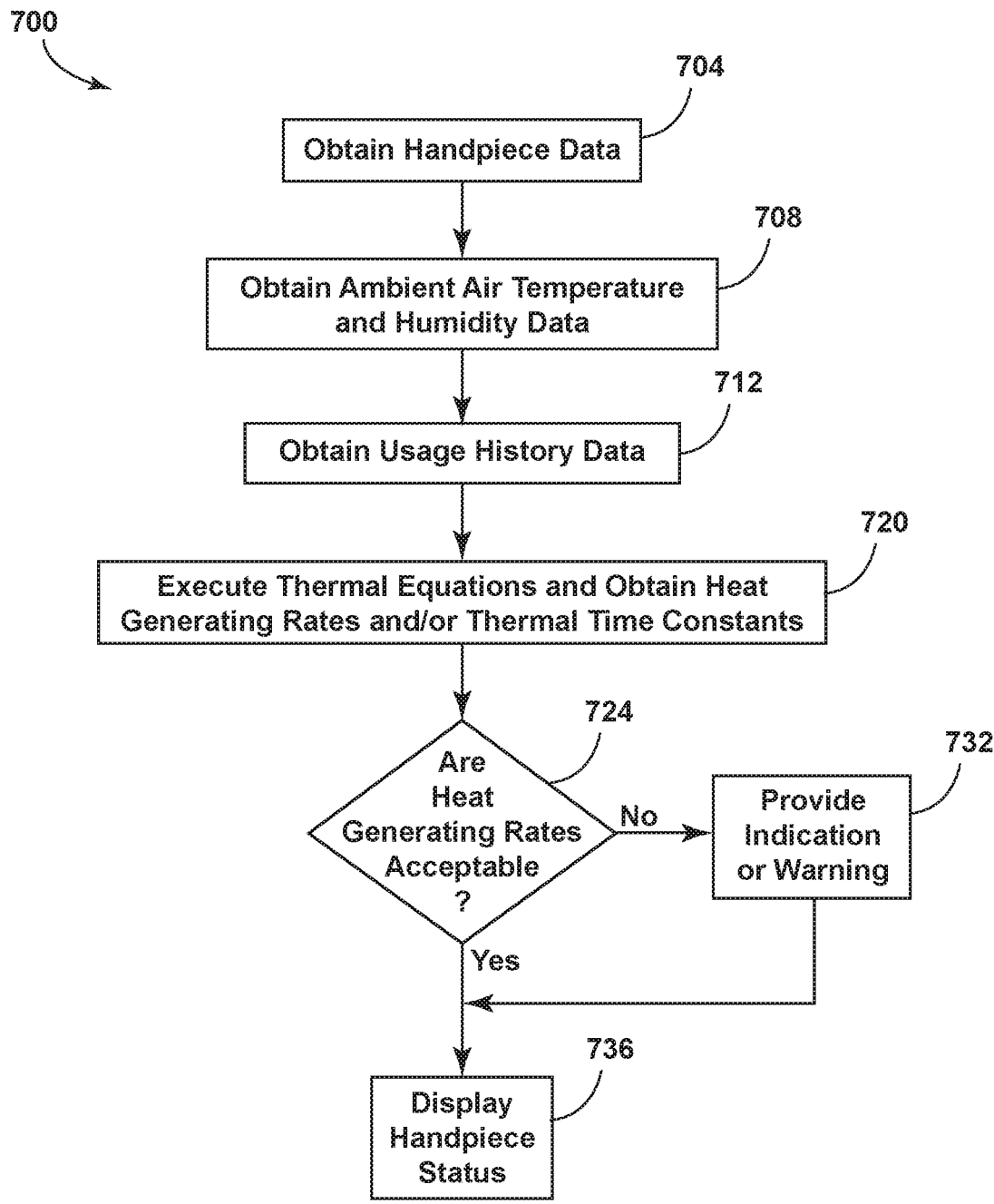
FIG. 12 is a flowchart of a method for providing predictive maintenance for a handpiece.

Another embodiment for predicting bearing failure or other maintenance conditions utilizes temperature data and other handpiece data for the handpiece 40. A processor or controller associated with one or more of the motor controller 24, a delivery unit 210, 240, a cloud computer 370, a portable universal controller 360, the treatment unit 200 or another device performs the method set forth in the flowchart 700 of FIG. 12.

To predict bearing failure, temperatures of one of the aforementioned components is measured and compared to data gathered from the handpiece's environment. In one example shown in FIG. 12, the method obtains handpiece data, such as handpiece operating speeds, handpiece operating times, handpiece vibration data, and temperature data for the handpiece 40 from condition sensors (step 704). Further, ambient air temperature and humidity conditions are obtained by the processor (step 708). The method then obtains previous handpiece usage history from the data logging equipment 310 (step 712). This data, and especially the temperature data, is executed by the processor through a series of thermal equations that calculate and obtain heat generating rates of the bearings/handpiece 40 and/or thermal time constants (step 720). The method sends this data to cloud storage or compares the heat generating rates locally with the history of previously calculated results for the handpiece 40 from the data logging equipment 310 (decision step 724). When an unacceptable variance from the calculated heat generating rates and/or the average of the last several calculated rate results for the same handpiece 40 is obtained, the method advances to provide an indication or warning recommending handpiece maintenance for the handpiece or a particular component thereof (step 732). When the heat generating rates are acceptable (decision step 724), the method advances directly to step 736.

Thereafter, an overall handpiece status is displayed (step 736 in FIG. 12) based not only on the calculated results, but a history of how the handpiece 40 has been used. This history is built, in large part, by the data gathered from the environment of the handpiece 40, along with the handpiece itself, and stored in the data logging equipment 310. The method of FIG. 12 may then be iterated multiple times to display handpiece status (step 736) and/or a warning (step 732).

Thermal Comparative Analysis

Another method is directed to thermal comparative analysis. In this embodiment, a comparison is made with data from other handpiece(s). This method also predicts bearing failure or other maintenance conditions, while utilizing temperature data and other handpiece data for the handpiece 40, along with handpiece data from other handpieces of the same model. A processor or controller associated with one or more of the motor controller 24, a delivery unit 210, 240, a cloud computer 370, a portable universal controller 360, the treatment unit 200 or another device executes the method set forth in the flowchart 800 shown in the embodiment of FIG. 13.

Figure 13:
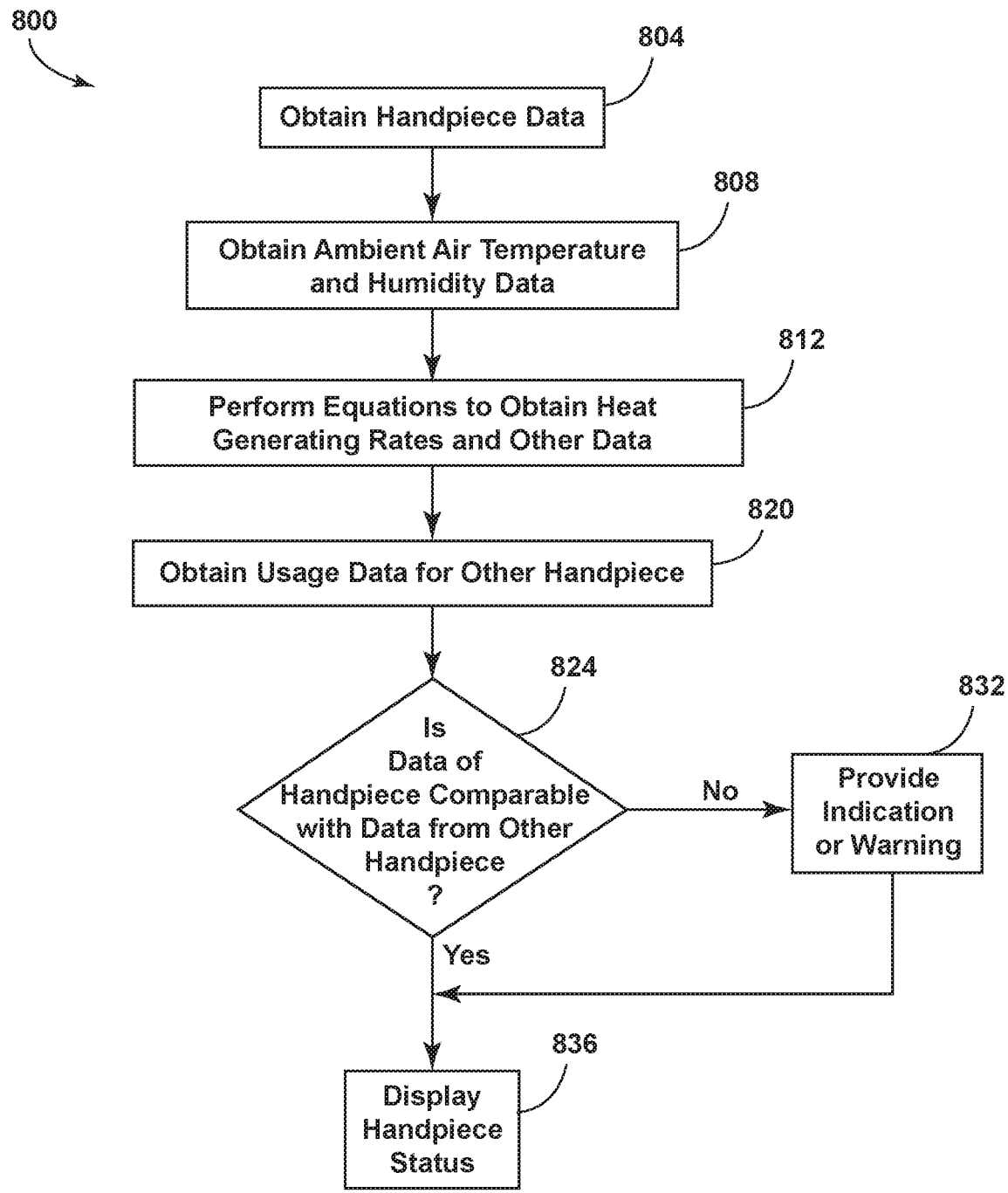
FIG. 13 is a flowchart of a method providing predictive maintenance for a handpiece by comparing sensor data with data from other handpieces.

In the example shown in FIG. 13, the method obtains handpiece data, such as handpiece operating speeds, handpiece operating times, handpiece vibration data, and temperature data for the handpiece 40 from condition sensors (step 804). Further, ambient air temperature and humidity conditions are obtained by the processor (step 808).

Then the handpiece data, and especially the temperature data for the handpiece 40, is executed by the processor through a series of equations for calculating heat generating rates of the bearings/handpiece 40 and/or thermal time constants (step 812) or other values for other sensors.

The method obtains historic usage data for one other handpiece of the same model or averaged data for a plurality of other handpieces of the same model handpiece that has previously been measured and stored, from cloud storage 370 or another memory (step 820).

A comparison is made between the generated data of the handpiece 40 and corresponding data from other handpiece(s) (step 824). When an unacceptable variance from the sensor data of the handpiece 40 and corresponding data for other handpieces result, the method advances to provide an indication or warning recommending handpiece maintenance for the handpiece or a particular component thereof (step 832). When the comparison with the data from another handpiece is acceptable (decision step 824), the method advances to step 836.

Thereafter, an overall handpiece status is displayed (step 836) based not only on the calculated results, but a history of how the handpiece 40 has been used. This history is built, in large part, by the data gathered from the environment of the handpiece 40, along with the handpiece itself, and stored in the data logging equipment 310. The method of FIG. 13 may then be iterated multiple times to display handpiece status (step 836) and/or a warning (step 832).

In one embodiment, the method is performed by a microcontroller 90 of a motor controller 24. The data compared is a heat generating rate directed to a temperature sensor for a bearing of the handpiece 40 that is based on the handpiece data including temperature data and the usage of the handpiece, along with ambient room conditions. Thus, thermal comparative analysis is performed between the temperature data and/or heat generating rate of the handpiece 40 and the stored temperature data and/or heat generating rate data of other handpieces of the same model.

Graphical User Interface

Figure 14:
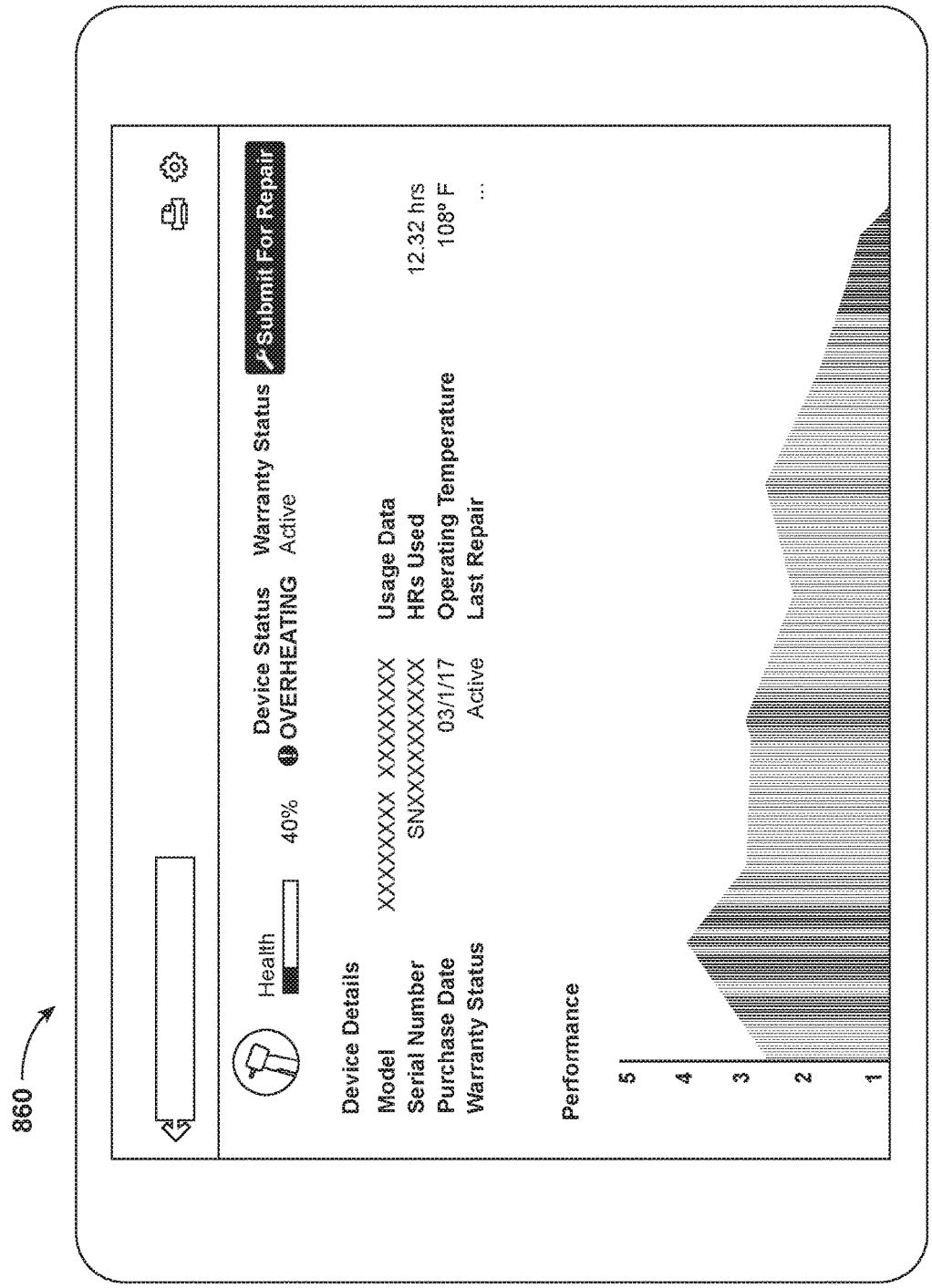
FIG. 14 shows a graphical user interface for a display of a delivery unit.

FIG. 14 shows a graphical user interface (GUI) 860 for conditions of a handpiece 40. The GUI 860 shows the model number and a unique serial number for the handpiece. Moreover, the GUI 860 shows a handpiece status of "OVERHEATING" and a health status of 40%. Further, the GUI 860 shows a total hours used of 12.32 hours and an operating temperature of 108 degrees Fahrenheit (F). Further, a graphical performance display of historical performance of the handpiece 40 over time is displayed as a graph at the lower part of the GUI 860. The graphical performance display has a scale from 1 to 5 with five being optimal performance. The overheating condition results in a lower value displayed on the right end of the bar graph. The bar graph includes various colors (not shown) relating to the performance thereof. The condition shown in FIG. 14 corresponds to an overheating warning or warning only stage as discussed with above respect to FIGS. 10 and 11. Further, if the operating temperature of the handpiece 40 increases to a critical level, handpiece shut down occurs and the GUI 860 will display information indicating the handpiece 40 is shutting down and may include an explanation why.

The analytics shown in FIGS. 10 and 11 and variations discussed above are performed in one or more of a delivery unit 210, 240, including the microcontroller 90 of the stand-alone handpiece system 20, a computer or processor associated with a treatment unit 200, a portable universal controller 360, a cloud computer 370 or a separate computer (not shown). For instance, in one embodiment the microcontroller 90 performs the operations shown in FIGS. 10 and 11 and also displays the handpiece usage data on the GUI 94.

Tool Wear

In addition to the temperature of the handpiece 40, another embodiment includes determining or sensing vibration data for the handpiece with the vibration sensor 74. The vibration data is processed and an alarm indication is provided when the vibration data values indicating a wear condition for a cutting tool secured to the handpiece 40. In one embodiment, the type of cutting tool mounted to the handpiece 40 is stored in the data logging equipment, along with the usage history thereof. Further, the type of operation procedure, including the type of tissue to be cut, is enterable by an operator. The system processes the vibration data value based on the additional information provided. In this embodiment, tool wear for the tool secured to the handpiece 40 is determined.

While FIGS. 3-5 show temperature sensors 60, 66, 70 for the drive assembly bearings, the temperature sensors are not limited to the bearings, but may also include components in contact with the bearing in which heat may transfer through, such as the bearing holding assembly, handpiece body or any one of the internal shafts. The temperature of these components may be measured by means of an internal temperature sensor disposed in the handpiece 40 or an external temperature sensor.

In one embodiment, a timestamp or time marker is digital data providing a date, hour, minute and milliseconds that a sensed value was obtained. The timestamp is associated with sensor data for a particular sensor, such as a temperature sensor, humidity sensor, or a vibration sensor. In other embodiments, the time stamp is also associated with handpiece motor conditions, While FIGS. 5 and 6 show a wired connection between sensors 60, 66 on the handpiece 40 and the microcontroller 90 of the motor controller 24, other embodiments are contemplated. For instance wireless RF, RFID, optical, acoustic or other methods are contemplated for providing information, including a device identifier and/or sensed data, from the handpiece 40 to the electronic processor of the motor controller 24.

Thus, the embodiments provide, among other things, a method of providing predictive maintenance for a dental handpiece 40 or component thereof, that includes sensing a condition of the handpiece with a condition sensor to obtain sensor data and providing wired communication of the sensor data and a device identifier from the handpiece to a delivery unit. The method includes storing the sensor data, the device identifier and a time stamp in data logging equipment to obtain a usage history for the handpiece, determining a maintenance condition of the handpiece based on the sensor data and/or the usage history of the handpiece, and in response to a severity of the maintenance condition, providing a preventative maintenance indication of a future failure for the handpiece. Various features and embodiments are set forth in the following claims.

What is claimed is:

1. A method of providing predictive maintenance for a dental handpiece or component thereof, comprising:
   sensing a bearing temperature of the handpiece with a bearing temperature sensor to obtain bearing temperature sensor data; and
   providing communication of the bearing temperature sensor data and a device identifier from the handpiece to a delivery unit;
   sensing handpiece operating speed and operating time, and providing communication thereof from the handpiece to the delivery unit;
   sensing ambient air temperature and/or humidity conditions for the handpiece from one or more external sensors, and providing communication thereof to the delivery unit;
   storing the bearing temperature sensor data, the device identifier, the handpiece operating speed and operating time, a time stamp, and ambient air temperature and/or humidity conditions for the handpiece in data logging equipment to obtain a usage history for the handpiece;
   determining a maintenance condition of the handpiece based on the bearing temperature sensor data and/or the usage history of the handpiece including calculating heat generating rates and/or thermal time constants for the handpiece based on the bearing temperature data, the handpiece operating speed and operating time, and the ambient air temperature and/or the humidity conditions, and
   in response to a severity of the maintenance condition, providing a preventative maintenance indication of a future failure for the handpiece,
   wherein an increased severity of the maintenance condition results in one or more from a group consisting of: a warning of an expected failure of the handpiece and a disabling of operation of the handpiece.

2. The method according to claim 1, including comparing the calculated heat generating rates and/or the thermal time constants for the handpiece with previously calculated and stored results for the handpiece.

3. The method according to claim 1, wherein determining the maintenance condition of the handpiece is further based on torque, at least one of an axial load and a radial load applied to an electric motor, and a power consumption of the electric motor.

4. The method according to claim 1, wherein the data logging equipment for storing the bearing temperature sensor data, the device identifier and the time stamp is a cloud server, the cloud server determining the severity of the maintenance condition of the handpiece.

5. The method according to claim 1, wherein the data logging equipment for storing the bearing temperature sensor data, the device identifier and the time stamp is a non-transitory memory of a delivery unit controller of the delivery unit.

* * * * *